United States Patent [19]
Kingwell

[11] Patent Number: 5,769,892
[45] Date of Patent: Jun. 23, 1998

[54] SURGICAL STAPLER SLEEVE FOR REINFORCING STAPLE LINES

[75] Inventor: Brian Gordon Kingwell, Vancouver, Canada

[73] Assignee: Mitroflow International Inc., Richmond, Canada

[21] Appl. No.: 734,787

[22] Filed: Oct. 22, 1996

[51] Int. Cl.[6] .............................. A61F 2/02; A61B 17/04
[52] U.S. Cl. ............................. 623/11; 606/151; 600/37; 227/178.1; 227/180.1
[58] Field of Search .......................... 623/2, 11; 606/148, 606/151, 156; 602/48, 50; 600/36, 37; 227/178.1, 180.1, 19

[56] References Cited

U.S. PATENT DOCUMENTS

| | | | |
|---|---|---|---|
| 2,143,910 | 1/1939 | Didusch | 128/335.5 |
| 3,496,940 | 2/1970 | Steinman | 128/335 |
| 3,633,582 | 1/1972 | Steinman | 128/334 |
| 3,665,927 | 5/1972 | Kurtz | 128/335.5 |
| 3,739,402 | 6/1973 | Cooley et al. | 3/1 |
| 3,983,581 | 10/1976 | Angell et al. | 3/1.5 |
| 3,988,782 | 11/1976 | Dardik et al. | 3/1 |
| 4,388,735 | 6/1983 | Ionescu et al. | 3/1.5 |
| 4,648,881 | 3/1987 | Carpentier et al. | 623/11 |
| 4,681,588 | 7/1987 | Ketharanathan | 623/11 |
| 4,930,674 | 6/1990 | Barak | 227/179 |
| 5,100,422 | 3/1992 | Berguer et al. | 606/151 |
| 5,141,144 | 8/1992 | Foslien et al. | 277/176 |
| 5,188,834 | 2/1993 | Grimm et al. | 424/422 |
| 5,222,974 | 6/1993 | Kensey et al. | 606/213 |
| 5,263,629 | 11/1993 | Trumbull et al. | 227/181 |
| 5,366,480 | 11/1994 | Corriveau et al. | 606/233 |
| 5,397,324 | 3/1995 | Carroll et al. | 606/139 |
| 5,487,500 | 1/1996 | Knodel et al. | 227/181.1 |
| 5,503,638 | 4/1996 | Cooper et al. | 623/11 |
| 5,542,594 | 8/1996 | McKean et al. | 227/178.1 |

OTHER PUBLICATIONS

Mitroflow International, "Peripatch Cylinders" borchure, pre–1996.
Perryman et al., "Pericardial Pledgets in Cardiac Surgery", Ann Thorac Surg 42:601–603, Nov. 1986.
Nakamura et al., "Clinical Applications of Bioabsorbable PGA Sheets for Suture Reinforcement and Use as Artificial Pleura", Japan Lung Surgery Journal 40:10, 8(1826), 1992.
Connolly et al., "The Current Status of Surgery for Bullous Emphysema", J. Thorac Cardiovasc Surg 1989, 351–61.
Juettner et al., "Reinforced Staple Line in Severely Emphysematous Lungs", J Thorac Cardiovasc Surg 1989, 97:362–3.
Lima et al., "Median Sternotomy for Bilateral Resection of Emphysematous Bullae", J Thorac Cardiovasc Surg 1981, 82:892–897.
Cooper, "Technique to Reduce Air Leaks After Resection of Emphysematous Lung", 1994, Ann Thorac Surg 1994; 57:1038–9.
Shapira, "An Alternative to Felt Pledgets in Cradiac Surgery", Ann Thorac Surg 41:219–221, Feb. 1986.

*Primary Examiner*—Gary Jackson

[57] ABSTRACT

A surgical stapler sleeve comprises a sheet of host-compatible material, a first edge of the sheet being folded back adjacent to a second edge of the sheet to give the sheet a tubular conformation, the first and second edges being releasably fastened to one another.

8 Claims, 4 Drawing Sheets

SURGICAL STAPLER SLEEVE FOR REINFORCING STAPLE LINES

FIELD OF THE INVENTION

The invention is in the field of surgical stapling. In particular, the invention relates to a sleeve adapted to work with a surgical stapler to reinforce surgical staple lines.

BACKGROUND OF THE INVENTION

Staples may be used in some surgical procedures to hold tissue layers together. Surgical staples, like many other kinds of staple, generally have two legs joined by a back, the legs being adapted to fold against the back when the staple is applied by a surgical stapler.

A variety of surgical staplers are known, such as the devices disclosed in the following U.S. Patents, which are hereby incorporated by reference: U.S. Pat. No. 5,487,500 to Knodel et al.; U.S. Pat. No. 4,863,088 to Redmond et al.; U.S. Pat. No. 5,141,144 to Foslien et al.; U.S. Pat. No. 4,633,874 to Chow et al.; and U.S. Pat. No. 4,520,817 to Green. Surgical staplers generally comprise opposed jaws: a cartridge jaw adapted to contain a staple cartridge with staples disposed in parallel rows, and an anvil jaw adapted to function as an anvil against which staples ejected from the cartridge jaw are deformed.

To use a surgical stapler, tissue to be stapled is inserted between the opposed jaws of the stapler. The stapler is actuated to eject the staples. The legs of the staples ejected from the cartridge jaw of the stapler first pass through the tissues to be stapled. The staples are then deformed as they are forced against the anvil jaw, bending the legs of each staple towards the back of the staple, so that the tissue is clamped between the legs and the back of each staple.

A knife is generally provided on one of the jaws of a surgical stapler; the knife being movable along the jaw to make a longitudinal incision between the rows of applied staples. The staples on either side of the incision clamp the edges of the severed tissue to prevent leakage of fluids from the severed edge.

Surgical staplers are useful in a wide variety of procedures. In some cases, particularly where the staples are to pass through weak tissue, it is desirable to reinforce the staple line, ie. to reinforce the engagement between the staples and the stapled tissues. Reinforcement of the staple line may reduce post-operative complications caused by tearing of stapled tissues or leakage of fluids such as blood or air through staple lines.

Staple lines may be reinforced by sandwiching the tissue to be stapled between layers of reinforcing material before applying the staples; when the staples are applied, the legs of the staple pass from the cartridge jaw through a first layer of reinforcing material, then through the patient's tissue, and finally through the other layer of reinforcing material before encountering the anvil jaw. With the staples in place, the stapled tissue is clamped between the layers of reinforcing material.

A variety of staple line reinforcements have previously been used: TEFLON felt, attached to staple jaws with adhesive strips, has been used as a staple line reinforcement in surgery for bullous emphysema (Connolly, J. E. and Wilson, A., The Current status of surgery for bullous emphysema, 1989, J. Thorac. Cardiovasc. Surg. 351:61); strips of polydioxanone ribbon have been used to reinforce staple lines for parenchymal stapling of emphysematous lungs (Juettner, F. M. et al., Reinforced staple line in severely emphysematous lungs, J. Thorac. Cardiovasc. Surg., 1989, 97:362); U.S. Pat. No. 5,503,638 to Cooper et al. discloses the use of animal tissue attached to a U-shaped buttress member as a soft tissue stapling buttress.

Surgical staplers are often used in resection procedures, in which the longitudinal incision between the rows of staples divides tissue that is to remain in the body from tissue that is to be excised. In such procedures, a first part of the reinforcing material is stapled to tissue that remains in the body and a second part of the reinforcing material is stapled to tissue that is excised; the longitudinal incision introduced by the stapler separates the first and second parts of the reinforcing material.

There is a need in the art for a surgical stapler sleeve for reinforcing staple lines that is simple to manufacture, easy to use and particularly convenient for use in resection procedures.

SUMMARY OF THE INVENTION

A surgical stapler sleeve for reinforcing staple lines may be made from a single sheet of host-compatible material. The host-compatible material may, for example, be fixed pericardium, such as tanned bovine pericardium. To form the sleeve, a first edge of the sheet is folded back adjacent to a second edge of the sheet, to give the sheet a tubular conformation. The adjacent first and second edges of the sheet are releasable fastened to one another, such as by suture, to form the tubular sleeve.

In use, a sleeve of the invention may be fitted to each of the opposed jaws of a surgical stapler. In resection procedures, a first part of the sleeve (the disposable part) may be stapled to the tissue to be removed, a second part of the sleeve (the retained part) will then be stapled to the tissue that is to remain in the patient. After the staples are applied, the stapler knife is used to introduce a longitudinal incision between the rows of staples. The incision separates the disposable part of the sleeve from the retained part of the sleeve, leaving the disposable part and the retained part attached to each other only by the releasable fastening between the first and second edges of the sheet. Releasing the fastening between the first and second edges of the sheet completely separates the disposable part of the sleeve from the retained part, leaving the retained part stapled to the tissue that is to remain in the patient and the disposable part stapled to the tissue that is to be removed from the patient. The disposable part of the sleeve may then be removed together with the tissue that is excised from the patient.

A sleeve may be mounted on a stapler with the joined edges of the sheet on one side of the stapler jaw, preferably adjacent to a staple line. A symbolic indication may be provided on the exterior of the tube formed by the sheet to help a user differentiate the two sides of the sleeve, ie. to differentiate the side of the sleeve having the releasably fastened first and second edges from the other side of the sleeve. In effect, the symbolic indication may be used to help the surgeon to properly orient the stapler so that the disposable part of the sleeve will be stapled to the tissue that is to be excised, and the retained part of the sleeve will be stapled to the tissue that remains in the patient.

The sleeves may be arranged on the stapler so that the fastened edges of the sheets are opposite one another, ie. the fastened edges of the two sleeves lie on the same side of the stapler. When the releasably fastened edges of the sleeves are positioned adjacent to the tissue that will remain in the patient, the retained parts of the sleeves will consist of a narrow strips of material, while the disposable parts of the sleeves will consist of the remaining majority of the sleeves. After stapling, incision and release of the fastenings between the first and second edges of the sleeves, the disposable parts of the sleeves may be removed along with the excised tissue to which they is stapled, leaving the strips of the retained part of the sleeves stapled to the patient's tissue along the line of the incision. Accordingly, it will be appreciated that the configuration of the sleeve of the invention provides for an elegantly simple surgical stapling procedure.

DETAILED DESCRIPTION OF THE PREFERRED EMBODIMENT

Figure 1:
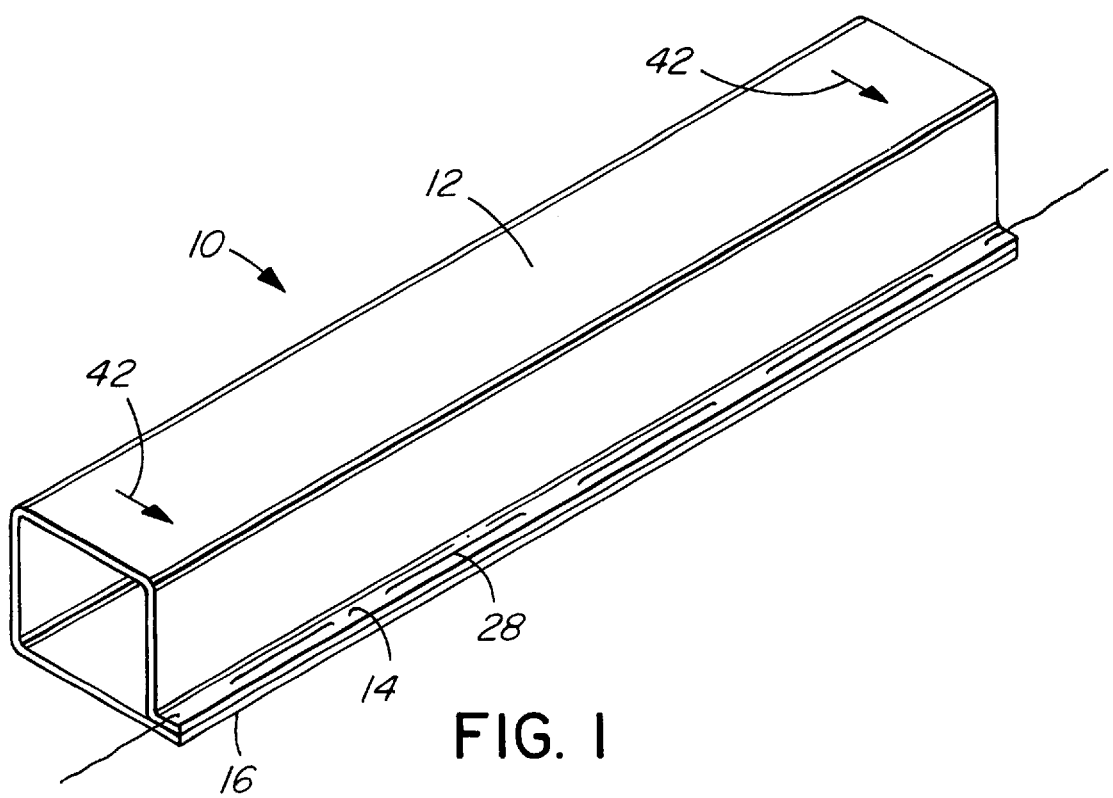
FIG. 1 is an isometric view of the sleeve of the invention.

Referring to FIG. 1, a surgical stapler sleeve 10 comprises a sheet 12 of host-compatible material, a first edge 14 of sheet 12 being folded back adjacent to a second edge 16 of sheet 12 to give the sheet 12 a tubular conformation, first 14 and second 16 edges being releasable fastened to one another, such as by suture 28.

Sleeve 10 may be made from a single sheet 12 of host-compatible material. "Host-compatible" means the material is acceptable for implantation into a surgical patient. The compatibility of a material for use in a host may be assessed by those skilled in the art of the invention, based on criteria such as toxicity and immunogenicity. Materials which may be host-compatible in particular applications include the following: fixed (cross-linked or tanned) animal tissue, such as bovine pericardium (U.S. Pat. No. 5,188,834 to Grimm et al., incorporated herein by reference, describes a method for fixing biological implantation material); or, polydioxanone ribbon (PDS-ribbon, Ethicon, Hamburg, Germany).

To form sleeve 10, a first edge 14 of sheet 12 is folded back adjacent to a second edge 16 of sheet 12, to give sheet 12 a tubular conformation. The conformation of the tube formed by sheet 12 may be adapted to closely match the shape of particular stapler jaws 18, 20.

To form tubular sleeve 10, adjacent first 14 and second 16 edges of sheet 12 are releasable fastened to one another. One or more sutures 28 may be used to sew edges 14, 16 together. If a single thread is used to fasten edges 14, 16, by weaving the thread alternatively between edges 14, 16, the end of the thread may be left trailing from sleeve 10 to facilitate removal of the suture thread simply by pulling on it. Glue or adhesive tape may be acceptable alternative means of releasably fastening together edges 14, 16. Other means of fastening may be acceptable, provided the attachment of edges 14, 16 is robust enough to withstand the stresses of normal use and the attachment is relatively simple to release when edges 14, 16 are to be separated.

In use, a sleeve 10 may be fitted to the opposed cartridge jaw 18 and anvil jaw 20 of a surgical stapler. Sleeves 10 may be arranged on stapler 22 so that releasably fastened edges 14, 16 of sheets 12 are opposite one another, ie. fastened edges 14, 16 of the two sleeves 10 lie on the same side of stapler 22.

In resection procedures, disposable part 30 of sleeve 10 may be stapled to tissue 34 that is to be removed from the patient, retained part 32 of sleeve 10 will accordingly be stapled to tissue 36 that is to remain in the patient. After staples are applied, stapler knife 38 is used to introduce a longitudinal incision between rows 40 of staples. The incision separates disposable part 30 of sleeve 10 from retained part 32 of sleeve 10, leaving disposable part 30 and retained part 32 attached to each other only by releasable fastening 28. Releasing fastening 28 completely separates disposable part 30 of sleeve 10 from retained part 32, leaving retained part 32 stapled to tissue 36 that is to remain in the patient and disposable part 30 stapled to tissue 34 that is to be removed from the patient. Disposable part 30 of sleeve 10 will then be removed when tissue 34 is excised from the patient.

Figure 3:
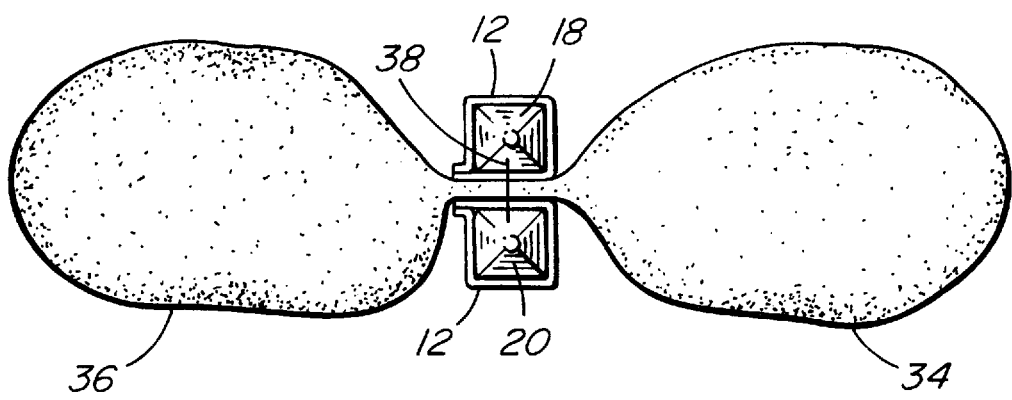
FIG. 3 is a front elevational view of sleeves mounted on stapler jaws holding tissue to be stapled.
Figure 2:
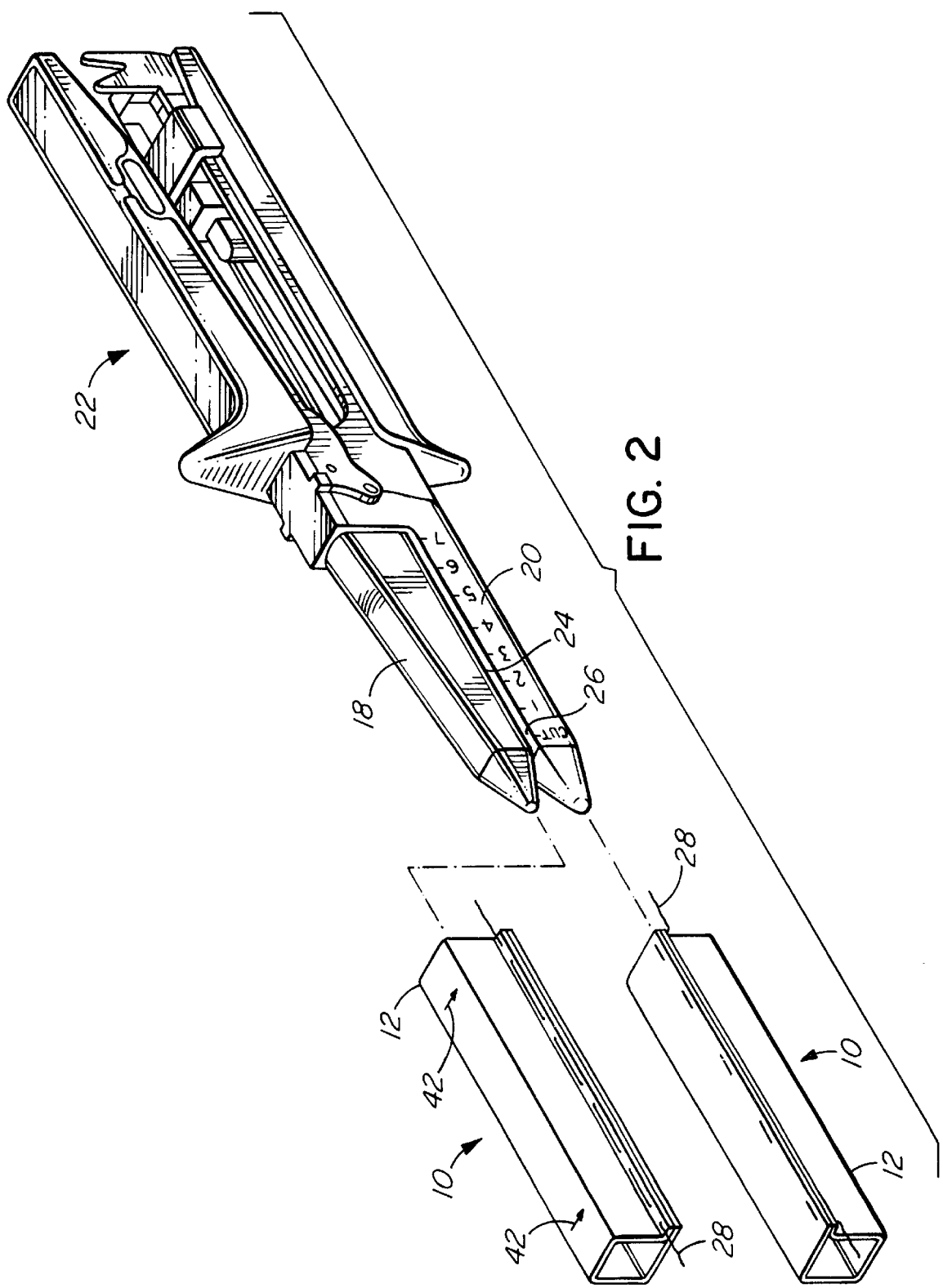
FIG. 2 is an isometric partially exploded view of sleeves oriented for mounting on a surgical stapler.
Figure 4:
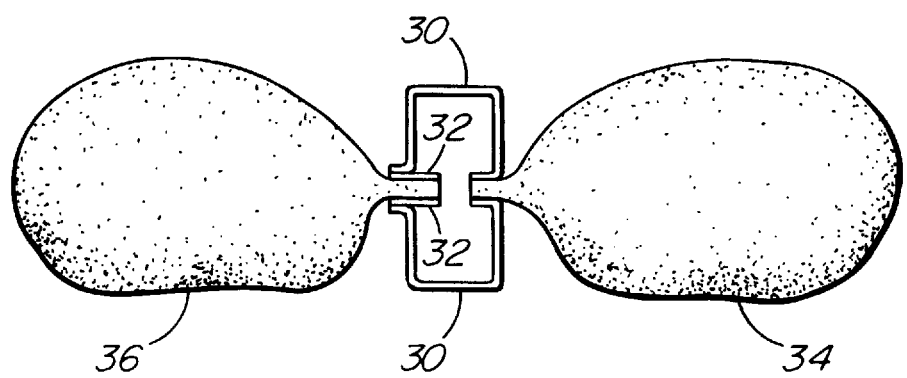
FIG. 4 is a front elevational view showing the retained parts and disposable parts of sleeves stapled to incised tissue, with the stapler removed from the sleeves.

As shown in FIGS. 2 and 3, sleeve 10 may be mounted on stapler 22 with first 14 and second 16 edges of sheet 12 disposed on the side of stapler jaws 18, 20, so that first 14 and second 16 edges will come to lie, adjacent to a row 40 of staples. A symbol 42 may be provided on the exterior of sheet 12 to help a user differentiate the two sides of sleeve 10, ie. to differentiate the side of sleeve 10 having releasably fastened first 14 and second 16 edges from the other side of sleeve 10. In effect, symbol 42 may be used to help a surgeon to properly orient stapler 22 so that disposable part 30 of sleeve 10 will be stapled to tissue 34 that is to be excised, while retained part 32 of sleeve 10 is stapled to tissue 36 that remains in the patient.

When sleeve 10 is positioned on stapler 22 as shown in FIGS. 2 and 3, retained part 32 of sleeve 12 will consist of a narrow strip of material, while disposable part 30 consists of the remaining majority of sheet 12. After stapling, incision and release of fastening 28, disposable part 30 may be removed along with the excised tissue to which it is stapled, leaving strips of retained part 32 stapled to the patient's tissue. Accordingly, it will be appreciated that the configuration of sleeve 10 provides for an elegantly simple surgical stapling procedure.

Figure 6:
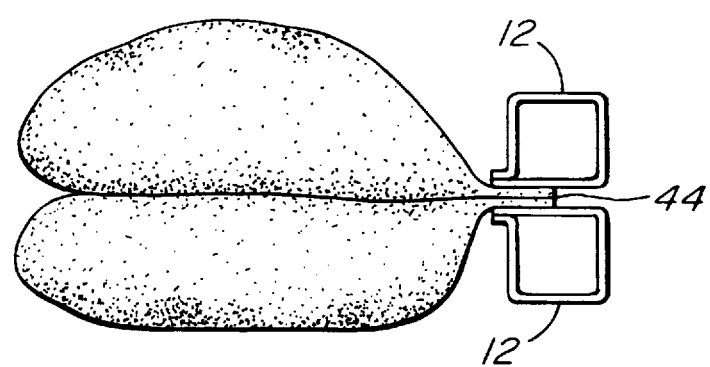
FIG. 6 is a front elevational view showing sleeves stapled to a tissue edge.
Figure 5:
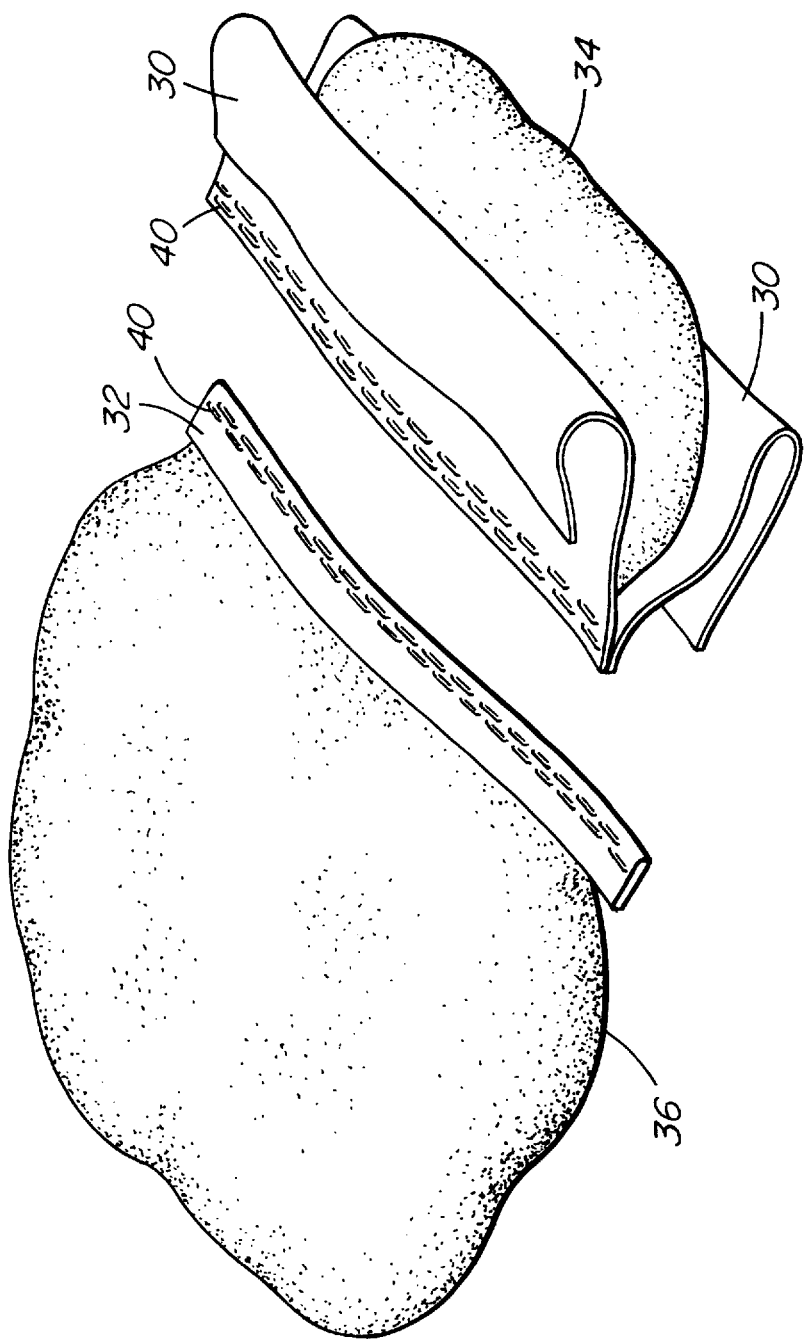
FIG. 5 is an isometric view showing the retained parts and disposable parts of sleeves stapled to incised tissue, after the sutures holding each of the sleeves together have been removed.

As shown in FIG. 6, the sleeve may of course be used to clamp tissue end 44 in cases where it is not necessary to resect any of the patient's tissue.

It will be appreciated by those skilled in the art that sleeve 10 is relatively simple to manufacture because it may be fabricated from a single sheet 12 of material and only one releasable fastening 28 needs to be installed to complete the tubular sleeve 10. This simplicity of manufacture is complemented by ease of use, since only a single releasable fastening 28 need be removed following stapling to separate disposable part 30 of sleeve 10 from retained part 32. Sleeve 10 is also safer to use than some prior art devices, because the whole sheet 12 is host-compatible, so that there is no risk that a non-compatible part of sleeve 10 could be stapled to the patient. These very important advantages distinguish the present invention over the Cooper et al. device disclosed in U.S. Pat. No. 5,503,638. Furthermore, because sleeve 10 is tubular, there is little risk that staples will miss sheet 12, a disadvantageous outcome which may occur with use of prior art strips of reinforcing material if the strips are forced out of position before stapler 22 is actuated.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A surgical stapler sleeve comprising a unitary sheet of host-compatible material formed into a tube with a generally planar longitudinal face, first and second longitudinal planar edges of the sheet being releasably fastened to one another next to the planar longitudinal face of the sleeve.

2. The sleeve of claim 1 wherein the first and second longitudinal edges of the sheet are releasably fastened by a suture.

3. The sleeve of claim 1 wherein the first and second longitudinal edges of the sheet are releasably fastened by an adhesive.

4. The sleeve of claim 1 wherein the host-compatible material is fixed pericardium.

5. The sleeve of claim 1 further comprising a symbol on the exterior of the sleeve, the symbol providing an indication of the location of the first and second longitudinal edges of the sheet.

6. A surgical stapler having jaws, with opposing generally planar jaw faces, and a knife, the knife and jaw faces being adapted to cooperate, when the stapler is actuated, to form an incision between at least two parallel longitudinal rows of staples emplaced between the jaw faces, comprising:

a first tubular sleeve formed from a unitary sheet of host-compatible material, the sleeve having a generally planar longitudinal face, the sleeve fitted around a first jaw of the stapler, with the planar longitudinal face of the sleeve on the planar jaw face of the first jaw of the stapler, first and second longitudinal planar edges of the sheet being releasably fastened to one another wherein said first edge is folded next to a longitudinal edge of the face of the first stapler jaw.

7. The surgical stapler of claim 6 further comprising a second tubular sleeve formed from a second unitary sheet of host-compatible material, the second sleeve having a generally planar longitudinal face, the second sleeve fitted around a second jaw of the stapler, with the planar longitudinal face of the second sleeve on the planar jaw face of the second jaw of the stapler, first and second longitudinal planar edges of the second sheet being releasably fastened adjacent to one another next to a longitudinal edge of the face of the second stapler jaw, the releasably fastened edges of the second sheet being opposed to the releasably fastened edges of the first sheet.

8. A method of reinforcing a surgical staple line comprising the steps of:

(a) providing a surgical stapler having jaws, with opposing generally planar jaw faces, and a knife, the knife and jaw faces being adapted to cooperate, when the stapler is actuated, to form an incision between at least two parallel longitudinal rows of staples emplaced between the jaw faces;

(b) fitting a first tubular sleeve formed from a unitary sheet of host-compatible material around a first jaw, the sleeve having a generally planar longitudinal face, with the planar longitudinal face of the sleeve on the planar jaw face of the first jaw of the stapler, adjacent longitudinal planar edges of the sheet being releasably fastened to one another next to a longitudinal edge of the face of the first jaw;

(c) fitting a second tubular sleeve formed from a second unitary sheet of host-compatible material around a second jaw, the second sleeve having a generally planar longitudinal face, with the planar longitudinal face of the second sleeve on the planar face of the second jaw of the stapler, adjacent longitudinal planar edges of the second sheet being releasably fastened to one another next to a longitudinal edge of the face of the second jaw, the releasably fastened edges of the second sheet being opposed to the releasably fastened edges of the first sheet;

(d) placing patient tissue between the sleeves on the jaws of the stapler;

(e) actuating the stapler to emplace at least two parallel longitudinal rows of staples between the jaw faces through the sleeves and the patient tissue;

(f) actuating the stapler knife to form an incision through the sleeves and the patient tissue between the rows of staples.

* * * * *